United States Patent [19]
Sutton et al.

[11] Patent Number: 5,231,985
[45] Date of Patent: Aug. 3, 1993

[54] DUAL CHAMBER RATE RESPONSIVE PACER

[75] Inventors: Richard Sutton, London, United Kingdom; Ivan Bourgeois, Vervier, Belgium; Loek Herpers, Kerkrade; Karl D. Dulk, Maastricht, both of Netherlands

[73] Assignee: Medtronic, Inc., Minneapolis, Minn.

[21] Appl. No.: 648,241

[22] Filed: Jan. 31, 1991

[51] Int. Cl.$^5$ ............................................. A61N 1/368
[52] U.S. Cl. ........................................ 607/18; 607/123
[58] Field of Search ................................. 128/419 PG

[56] References Cited

U.S. PATENT DOCUMENTS

| | | | |
|---|---|---|---|
| 4,429,697 | 2/1984 | Nappholz et al. | 128/419 PG |
| 4,467,810 | 8/1984 | Vollmann | 128/419 PG |
| 4,554,921 | 11/1985 | Boute et al. | 128/419 PG |
| 4,712,555 | 12/1987 | Thornander et al. | 128/419 PG |
| 4,712,556 | 12/1987 | Baker, Jr. | 128/419 PG |
| 4,722,341 | 2/1988 | Hedberg et al. | 128/419 PG |
| 4,856,523 | 8/1989 | Sholder et al. | 128/419 PG |
| 4,945,909 | 8/1990 | Fearnot et al. | 128/419 PG |
| 5,007,422 | 4/1991 | Pless et al. | 128/419 PG |
| 5,085,215 | 2/1992 | Nappholz et al. | 128/419 PG |
| 5,086,774 | 2/1992 | Duncan | 128/419 PG |

OTHER PUBLICATIONS

Rate-Responsive Dual-Chamber Pacing by Kappenberger et al., published in *New Perspectives in Cardiac Pacing*, edited by S. Serge Barold, MD et al., Futura Publishing Co., 1988.

Rate Responsive Dual Chamber Pacing, by Kappenberger et al., published in PACE, vol. 9, Nov.-Dec. 1986, Part II.

*Primary Examiner*—Kyle L. Howell
*Assistant Examiner*—Kennedy J. Schaetzle
*Attorney, Agent, or Firm*—S. A. Kassatly; Harold R. Patton

[57] ABSTRACT

A cardiac pacemaker and related pacing method. The cardiac pacemaker includes atrial and ventricular sense amplifiers for generating atrial and ventricular sense signals. An activity control circuit measures the activity level and initiates an activity interval. A control circuit responds to the atrial sense signals, the ventricular sense signals, and the activity control circuit, for controlling the atrial and ventricular stimuli generation, by matching the activity interval with the depolarization of the atrial tissue, in order to differentiate true exercise induced sinus tachycardia from atrial arrhythmias and retrograde atrial events, and to permit a selective ventricular rate control. The control circuit initiates a 2 to 1 ventricular to atrial response when the activity interval is greater than a VV interval, which is the sum of the interval between the last sensed or paced ventricular event and the atrial intrinsic depolarization ($VA_S$ interval) and the programmed AV delay or the sensed AV interval. The 2 to 1 block mode is induced by prolonging the post ventricular atrial refractory period (PVARP) for the next beat.

13 Claims, 4 Drawing Sheets

DUAL CHAMBER RATE RESPONSIVE PACER

BACKGROUND OF THE INVENTION

1. Field of the Invention

The present invention generally relates to cardiac pacers, and more particularly to a dual chamber rate responsive pacemaker which uses activity sensing to differentiate true exercise induced sinus tachycardia from atrial arrhythmias and retrograde atrial events, and to permit a selective ventricular rate control.

2. Background Art

Early pacemakers were asynchronous (VOO), and they stimulated the heart at a fixed rate, independent of the patient's underlying cardiac rhythm or metabolic demand. Although such pacers, typified by U.S. Pat. No. 3,057,356 to Greatbatch, provide a ventricular pacing rate sufficient to sustain life, this pacing mode can compete with native ventricular rhythms which is undesirable.

Subsequently, demand pacemakers (VVI) were developed. This type of pacer interacts with the patient's heart to provide stimulating pulses only if spontaneous cardiac activity does not occur. An example of such a pacer is taught by U.S. Pat. No. 3,478,746 to Greatbatch. This form of pacer provides a ventricular sense amplifier for detecting ventricular depolarizations. A ventricular sense event resynchronizes the pacer's V-V timer by resetting and restarting it. The ventricular sense event also cancels or inhibits the scheduled ventricular stimulus and thus avoids competition with the native ventricular rhythm.

Atrial synchronized pacers (VAT) were developed almost simultaneously with VVI demand pacemakers. This type of pacer paces the ventricle in response to the detected atrial rate of the patient. The VAT pacer, as typified by U.S. Pat. No. 3,253,596 to Keller, provides an atrial sense amplifier for detecting atrial depolarizations. An atrial sense event starts the pacer's A-V delay timer. When the A-V timer times out, a ventricular stimulus is provided. Conceptually, such a pacer can be considered as a prosthetic conduction pathway which simulates the natural A-V conduction pathways of the heart. One drawback to this form of pacing is its ability to compete with ectopic ventricular activity. An ectopic ventricular beat (PVC) may be detected in the atrium which will result in the generation of a ventricular stimulus a short time after the ventricular depolarization. Although such a pacing regime is considered harmless if the A-V delay is short, it is possible to deliver the pacing stimulus into the vulnerable period of the ventricle if a premature ventricular contraction occurs, and thereby initiate an arrhythmia.

Continued development of pacemakers was marked by the invention of the AV sequential pacer (DVI), as disclosed in U.S. Pat. No. 3,595,242 issued to Berkovits. This form of pacer provides for stimulation in both the atria and the ventricles while providing sensing in the ventricle. In this DVI mode pacer, a ventricular sense event starts both a V-A escape interval, the pacer delivers an atrial stimulus, and at the end of the V-V escape interval, the pacer delivers a ventricular stimulus. If a ventricular sense event occurs during the V-A or V-V time intervals, the pacer will resynchronize to the ventricular sense event and inhibit the delivery of the otherwise scheduled ventricular stimulus.

The DDI mode pacer described by U.S. Pat. No. 3,747,604 to Berkovits further includes an atrial sense amplifier to inhibit the atrial stimulus if an atrial sense event occurs during the V-A interval. The atrial sense event does not resynchronize the pacer which makes this device especially suitable in patients where atrial competition must be avoided.

The atrial synchronized ventricular inhibited or VDD mode pacer, as disclosed in U.S. Pat. No. 3,648,707 issued to Greatbatch has structures for sensing in the atrium and ventricle but provides stimulating pulses only in the ventricle. In operation, the VDD pacer will synchronize on detected atrial activity and provide a ventricular stimulus if one does not occur within the A-V delay initiated by the atrial depolarization. Ventricular sense events inhibit the delivery of the otherwise scheduled stimulus and resynchronize the pacer's V-V timer.

The dual sense—dual pace DDD mode pacers, have been described in U.S. Pat. No. 4,312,355 to Funke. The DDD pacer addresses many of the shortcomings of the prior art devices. The DDD mode pacer, as described by Funke, has had wide applications. This type of pacer has sense amplifiers for detecting both atrial and ventricular events, as well as output pulse circuits for stimulating both the atrium and the ventricle.

This form of prior art pacer provides timing circuitry to initiate an A-V delay upon the occurrence of an atrial event. If, during the A-V delay period, no spontaneous ventricular event is sensed, the pacer will produce a ventricular stimulus at the conclusion of the A-V delay period. If, during the V-A interval, no spontaneous atrial event is sensed, the pacer will produce an atrial stimulus at the conclusion of the V-A interval.

In this type of pacemaker, in the absence of spontaneous P waves and R waves, the heart will be stimulated at fixed AA and VV intervals with a fixed AV delay. However, if the ventricle depolarizes spontaneously, then the A-V is truncated and the observed A-A interval is not fixed and will be shorter than the arithmetic sum of the programmed A-V and V-A intervals.

The dual chamber modalities, DVI, VAT, VDD and DDD, have proven to be especially efficacious pacemakers since they restore A-V synchrony and thus improve cardiac output by accommodating the hemodynamic contribution of the atrial chambers within the pacing regime. The latter three modes also synchronize the pacing rate to the patient's native atrial or sinus rate and thus provide an increased pacing rate in response to bodily activity. Increasing cardiac rate is the major contributor to increased cardiac output.

More recently, other pacers which increase cardiac output in response to exercise have been proposed. They include pacemakers which rely upon the sensing of a historical average of atrial activity, blood pH, respiratory rate or QT interval data to alter the pacemaker's escape interval. A discussion of these background proposals may be found in "The Exercise Responsive Cardiac Pacemaker", IEEE Transactions on Biomedical Engineering, Vol. 12, December 1984.

One approach which is important to the understanding of the present invention is the activity responsive pacer described in U.S. Pat. No. 4,428,378, issued to Anderson et al, and which is incorporated by reference. The pacer disclosed in that patent monitors the physical activity of the patient and increases the pacing rate in response to increasing patient activity.

Other publications that provide background information for the operation of the present invention include U.S. Pat. No. 4,890,617 issued to Markowitz et al. which is incorporated herein by reference. This patent describes a dual chamber activity responsive pacemaker which senses and paces in both the atrium and the ventricle. The pacing rate is determined by the sensed activity of the patient, the programmed lower rate, and the patient's atrial or sinus rate.

U.S. Pat. No. 4,932,046, entitled "Dual Chamber Rate Responsive Pacemaker", assigned to Medtronic, Inc. of Minneapolis, Minn., which is incorporated herein by reference, describes a dual chamber rate responsive pacemaker. The pacemaker operates in an atrial synchronized modality when the sensed atrial rate is within a physiological range, and paces at a sensor-determined rate when the atrial rate is above or below the physiological range.

The Goy et al. article "Rate Response Dual Chamber Pacing" in Centro Editoriale Italiano, 1986, pages 60-65 describe in general terms, the clinical results of a rate responsive dual chamber pacemaker.

BRIEF SUMMARY OF THE INVENTION

It is one object of the present invention to disclose a pacemaker which simultaneously offers dual chamber pacing (DDD Mode) and activity controlled rate response. The pacemaker uses activity-sensing to differentiate true exercise induced sinus tachycardia from atrial arrhythmias and retrograde atrial events, and to permit a selective ventricular rate control.

Briefly, the above and further objects and features of the present invention are realized by a cardiac pacemaker and a related pacing method. The cardiac pacemaker includes an atrial sense amplifier for generating atrial sense signals in response to the depolarization of the atrial tissue. A ventricular sense amplifier generates ventricular sense signals in response to the depolarization of the ventricular tissue. An AV delay timer responds to the atrial sense amplifier for initiating an AV delay interval. An atrial stimulator generates atrial stimuli, and a ventricular stimulator generates ventricular stimuli.

An activity control circuit measures the activity level and initiates an activity interval. A control circuit responds to the atrial sense signals, the ventricular sense signals, and the activity control circuit, for controlling the atrial and ventricular stimuli generation by the atrial and ventricular stimulator, respectively by matching the activity interval with the depolarization of the atrial tissue, in order to differentiate true exercise induced sinus tachycardia from atrial arrhythmias and retrograde atrial events, and to permit a selective ventricular rate control.

The control circuit initiates a 2 to 1 ventricular to atrial response by prolonging the post ventricular atrial refractory period when the activity interval is greater than a VV interval, which is the sum of the interval between the last sensed or paced ventricular event and the atrial intrinsic depolarization ($VA_S$ interval) and the programmed AV delay or the sensed AV interval.

The method for cardiac pacing includes the steps of determining whether a P wave has been sensed; comparing the activity interval and the VV interval; and, if the activity interval is greater than the VV interval, then comparing the interval between the two previous atrial paced or sensed events, (PP interval) and the pacemaker maximum synchronization interval.

The pacemaker is then caused to pace in a 2 to 1 block mode if the PP interval is less than the maximum synchronization interval, and to pace in a 1 to 1 synchronous mode if the PP interval is greater than, or equal to, the maximum synchronization interval.

BRIEF DESCRIPTION OF THE DRAWINGS

The above and other objects and features of the present invention and the manner of attaining them, will become apparent, and the invention itself will be best understood, by reference to the following description and the accompanying drawings, wherein.

DESCRIPTION OF THE PREFERRED EMBODIMENT

The general concept of integrating activity sensing and dual chamber pacing in a pacemaker is published and generally described in "Rate Responsive Dual Chamber Pacing", PACE Journal, Vol. 9, November-December 1986, Part II, pages 987-991, by Lukas J. Kappenberger and Loek Herpers.

The authors of this article recognize that the use of pacemakers which reestablish or maintain atrioventricular synchrony is limited, due to the fact that many patients with AV conduction disturbances have additional sinus disease. Event though the use of a single chamber rate-responsive atrial pacemaker is possible in patients with sick sinus syndrome, sick sinus syndrome patients have, or may develop, additional AV-node disease, and require the use of a dual chamber rate responsive pacemaker.

Additionally, conventional rate responsive pacemakers are not without their inherent problems, in that rate-responsive ventricular pacing does not protect against the hemodynamic problems that can arise with the loss of timed atrial systole. Pacemaker syndrome and palpitations due to retrograde conduction have not yet been satisfactorily addressed.

Figure 1:
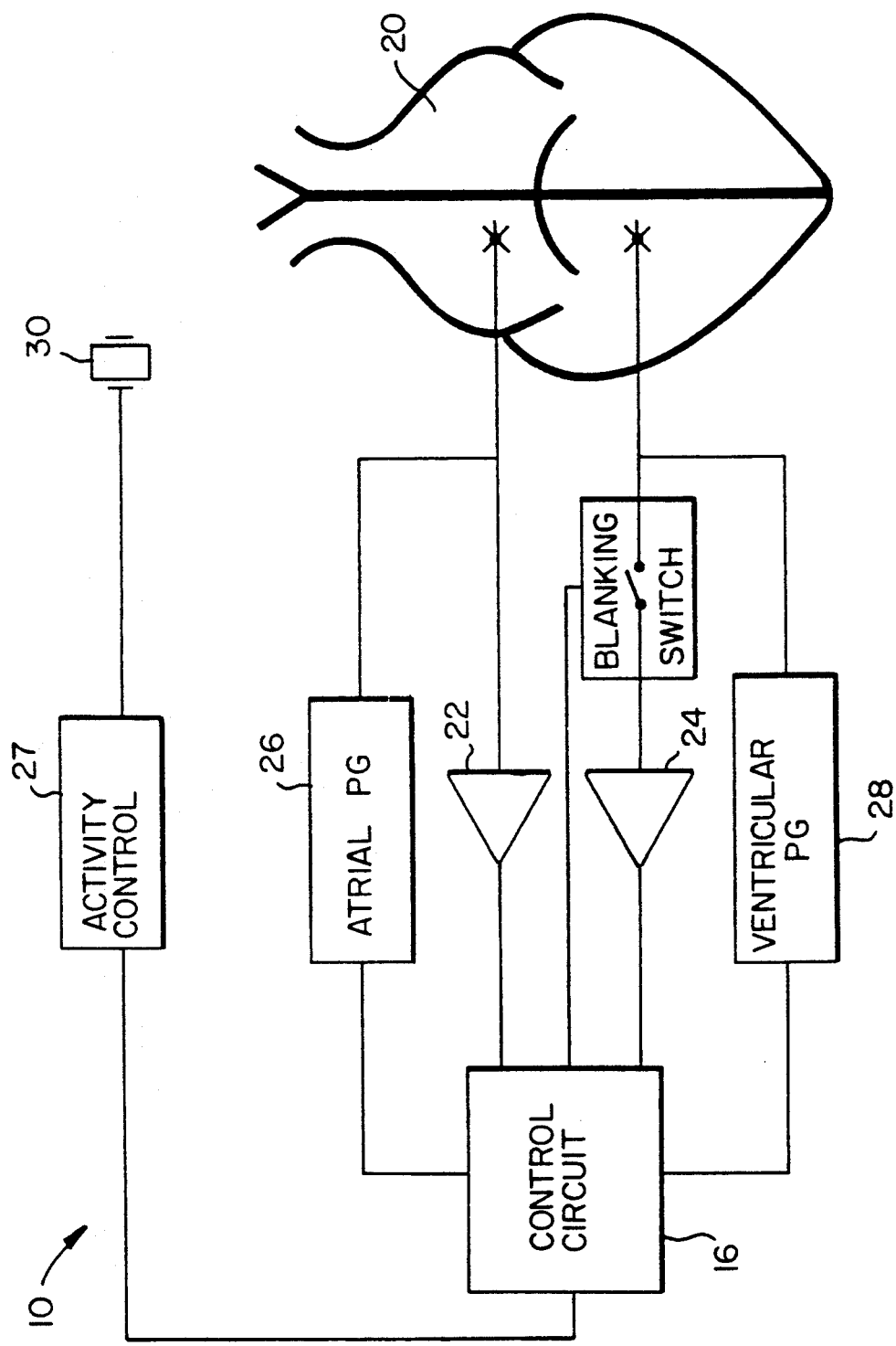
FIG. 1 is a block diagram of a pacemaker according to the present invention.

FIG. 1 illustrates the main elements of a pacemaker 10 according to the present invention. The pacemaker 10 can be either external or implantable. The pacemaker 10 generally includes an atrial sense amplifier 22, an atrial pulse or output generator 26, a ventricular sense amplifier 24, a ventricular pulse or output generator 25, a control circuit 16, an activity control circuit 27 and an activity sensor 30.

With the exception of the interface control circuit 16, the circuit designs of the pacemaker 10, can be adapted from circuit designs of conventional rate responsive and DDD pacemakers. The operation of the interface control circuit 16 will be described hereinafter in greater detail.

Hardware suitable for practicing the present invention includes Medtronic's Activitrax (R) pulse generators Models 8400, 8402 and 8403, and Medtronic's Symbios (R) Models 7005 and 7006. The pacemaker 10 is a programmable computer based unit which interfaces with the heart 20 through the atrial and ventricular sense amplifiers 22 and 24 respectively, as well as through the atrial and ventricular pulse or output generators 26 and 28 respectively. U.S. Pat. No. 4,577,633, which is incorporated by reference, describes one possible computer driven stimulator which can be used to practice the present invention. This patent is incorporated herein by reference.

The sensor 30 measures the metabolic demand of the patient. A suitable sensor is disclosed in U.S. Pat. No. 4,428,378 to Anderson and Brumwell, which sets forth the structure for monitoring the physical activities of the body to set a pacing rate. This patent is incorporated herein by reference.

The following Table I summarizes the operation logic of the novel pacemaker 10:

TABLE I

BRIEF SUMMARY OF OPERATION LOGIC

| Event | P Wave Sensing | Activity Interval/ DDD Intervals | Mode of Operation |
|---|---|---|---|
| 1. | No | Activity Interval ≤ VA Interval | DVIR - DDIR |
| 2. | No | Activity Interval > VA Interval | DDD/DDI at LR |
| 3. | Yes PP Rate ≤ ATUR | Activity Interval ≤ VV Interval | VDD - 1:1 Synchrony |
| 4. | Yes PP Rate > ATUR | Activity Interval ≤ VV Interval | VDD - Wenckebach at UR |
| 5. | Yes PP Interval ≥ Max. Synchronization Interval | Activity Interval > or ≤ VV Interval | VDD - 1:1 Synchrony |
| 6. | Yes PP Interval < Max. Synchronization Interval | Activity Interval > VV Interval | VDD - 2:1 Block |

The pacemaker 10 can be programmed to operate as a dual chamber demand pacemaker (DDD) without backup pacing rate control by means of activity sensing, at a demand responsive rate varying between a programmable lower rate ranging, for instance, between 50 and 90 pulses per minute (ppm), and a programmable atrial tracking upper rate (ATUR) ranging, for instance, between 125 and 175 ppm. When the pacemaker 10 paces at the atrial tracking upper rate, it operates in Wenckebach mode.

Once the pacemaker 10 is programmed in the DDD and activity modes according to the present invention, it operates in a substantially similar way to a conventional DDD pacemaker, with the exception that pacing in both the atrial and ventricular chambers is continuously regulated by the body activity detection circuitry within the range defined by the programmed basic rate (i.e. 60-70 ppm) and the programmed maximum activity rate (i.e. 120-140 ppm).

Figure 3:
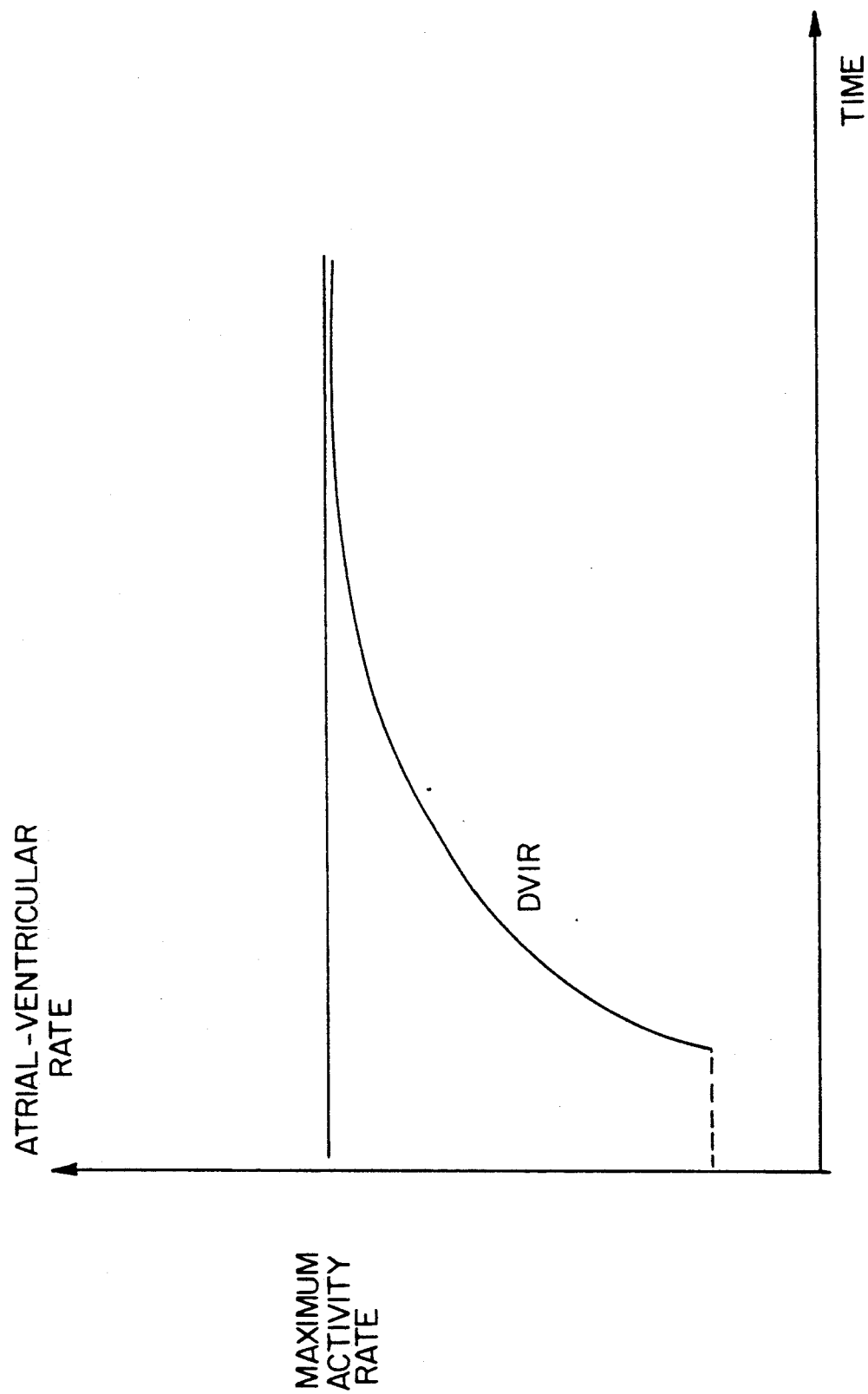
FIG. 3 is an exemplary rate diagram of the pacemaker of FIG. 1 showing the variation of the atrial—ventricular rate with time, as a function of activity.

FIG. 3 illustrates an exemplary rate diagram of the pacemaker 10, and shows the variation of the atrial—ventricular rate with time, as a function of activity. The atrial tracking upper rate (ATUR) and the programmed maximum activity rate can be separately programmable to provide the physician more flexibility in programming the pacemaker. The physician is able to select different values for the ATUR and the maximum activity rate.

Atrial synchronized ventricular pacing (VDD) up to the upper rate (UR) will be obtained if the interval between the last sensed or paced ventricular event and the atrial intrinsic depolarization ($VA_S$ interval) is shorter than the interval set by the activity sensor, and if the activity interval is shorter than the sum of the $VA_S$ interval and the programmed AV delay or sensed AV interval.

However, if the activity interval is longer than the sum of the $VA_S$ interval and the programmed AV delay or sensed AV interval, then the control circuit 16 will cause the atrial and ventricular pulse generators 26 and 28 to switch to an atrio-ventricular response of 2 to 1, such that a ventricular synchronized stimulus is generated for every other P wave, when the P rate is above a programmable maximum synchronization rate (i.e. 90 to 120 ppm). If on the other hand, the P rate is below or equal to the maximum synchronization rate, the atrio-ventricular response is synchronized (i.e. 1 to 1).

Consequently, the pacemaker 10 shows a unique feature in that it uses activity sensing to differentiate true exercise induced sinus tachycardia from atrial arrhythmias and retrograde atrial events, and to permit a selective ventricular rate control.

It is desirable to cause a rapid P-wave synchronized ventricular pacing to be possible only in the presence of activity detection. This behavior is achieved by causing the atrial and ventricular pulse generators 26 and 28 to switch to different synchronization modes, for preventing pacemaker reentrant tachycardia. As a result, the pacemaker 10 restores most of the physiologic cardiac rhythm with optimal hemodynamic improvement and thus optimal benefit to the patient.

The conversion of body activity to rate response is achieved by transforming the body's internal pressure changes into changes in atrial and ventricular pacing rates. This is achieved by using a piezoelectric element similar to the sensor used in the Medtronic Activitrax (R) pulse generator. These modifications allow continuous control of the backup rate of DDD pacing through the activity sensor, and therefore permit rate-responsive dual chamber pacing (DDDR).

The pacemaker 10 can be programmed using a Medtronic 9710 programmer. The programmable parameters are: mode (VOO, VVI, DOO, DVI, DDD), activity (yes/no), basic rate, AV interval, activity threshold, rate of response, atrial refractory period, pulse width A and V, pulse amplitude A and V, and sensitivity in A and V.

The operation logic of the pacemaker 10, illustrated in Table I, will now be described in detail, in relation to the flickered 200 of FIG. 2, and the rate diagram 800 of FIG. 5.

Figure 2:
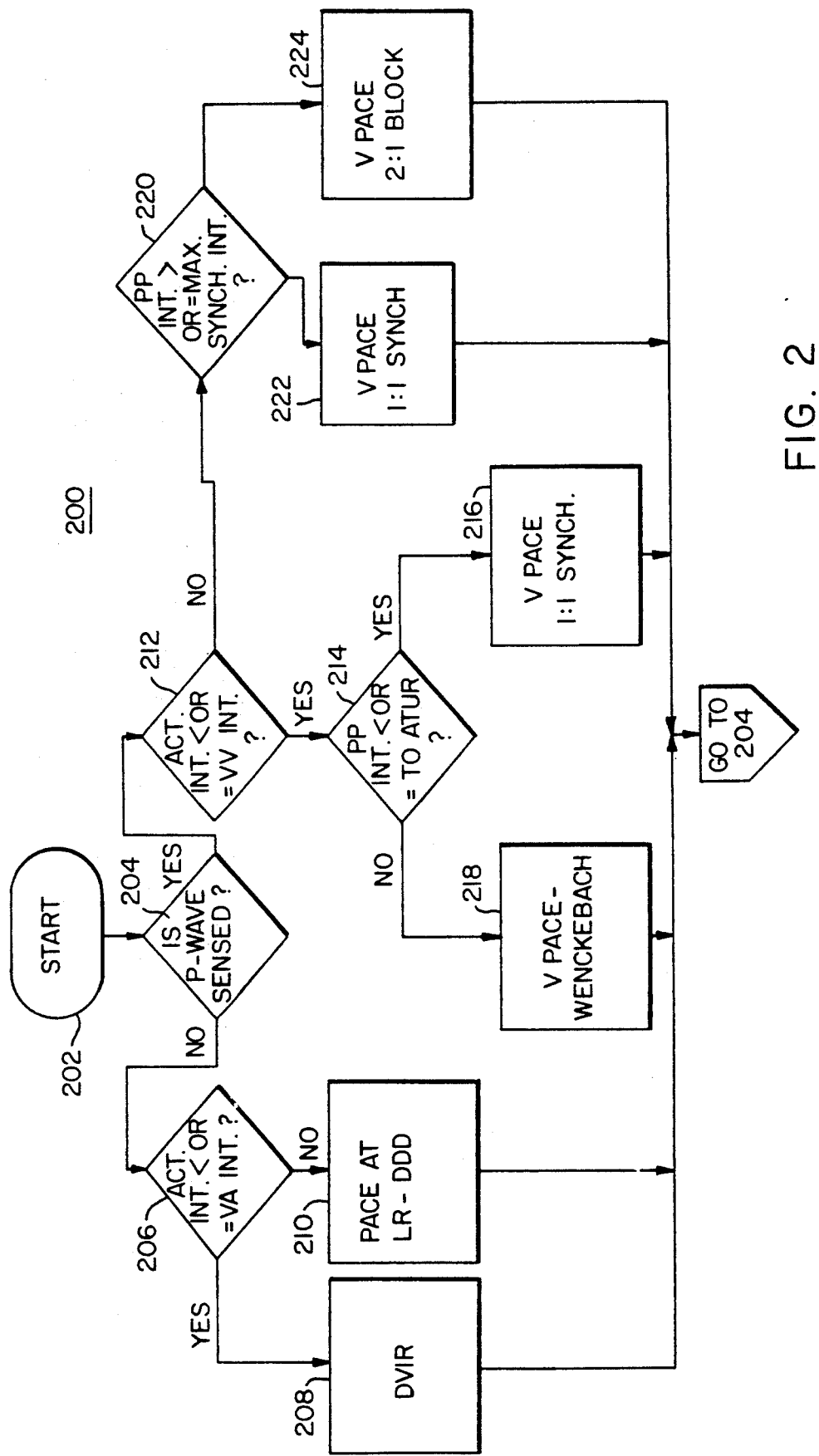
FIG. 2 is a software flickered illustrating the general operation logic of the pacemaker of FIG. 1 according to the present invention.

The software program illustrated by the flickered 200 of FIG. 2 is initiated at 202 by a ventricular event, and an inquiry is made at 204, whether atrial depolarization has been sensed. If it has not, then a determination is made at 206 whether the activity interval is shorter than, or equal to, the pulse generator programmed VA interval. A ventricular event resets the activity timer and the VA counter. A sensed or paced atrial event resets the AA counter and the AV counter.

If the activity interval is shorter than, or equal to, the programmed VA interval, then the pacemaker 10 operates in the DVIR mode (AV sequential pacing), or DDIR mode as illustrated by block 208, and by Event 1 in Table I. If on the other hand, the activity interval is longer than the programmed VA interval, then the pacemaker 10 will pace at the programmed lower rate (LR) in a DDD mode, as indicated by block 210 and Event 2.

If at block 204 a P-wave is sensed, then the activity interval is compared to a VV interval. As used herein, the VV interval is defined as the sum of the VA$_S$ interval and the programmed AV delay, or, alternatively, as the sum of the VA$_S$ interval and the sensed AV interval.

If the activity interval is less than, or equal to the VV interval, then the control circuit 16 compares the PP rate to ATUR, as indicated by block 214. As used herein, the PP interval refers to the interval between the previous atrial paced or sensed event, and the atrial depolarization.

If at 214 it is determined that the PP rate is lower than or is equal to ATUR, then, as indicated by block 216, 1 to 1 tracking will prevail, until the PP rate is higher than ATUR block 218), at which time the pacemaker 10 will slow its rate of ventricular pacing by the Wenckebach operation, 2 to 1 block, or another appropriate block. In a DDD pacemaker, the Wenckebach mode is an operational function which limits the average ventricular pacing rate when the intrinsic atrial rates rise above the programmed upper rate. The pacemaker does this by gradually prolonging the pacemaker's AV interval until one of the atrial events falls into the atrial refractory period and is not sensed. Since no AV interval is started, there will be no ventricular output synchronized to this atrial event.

Figure 4:
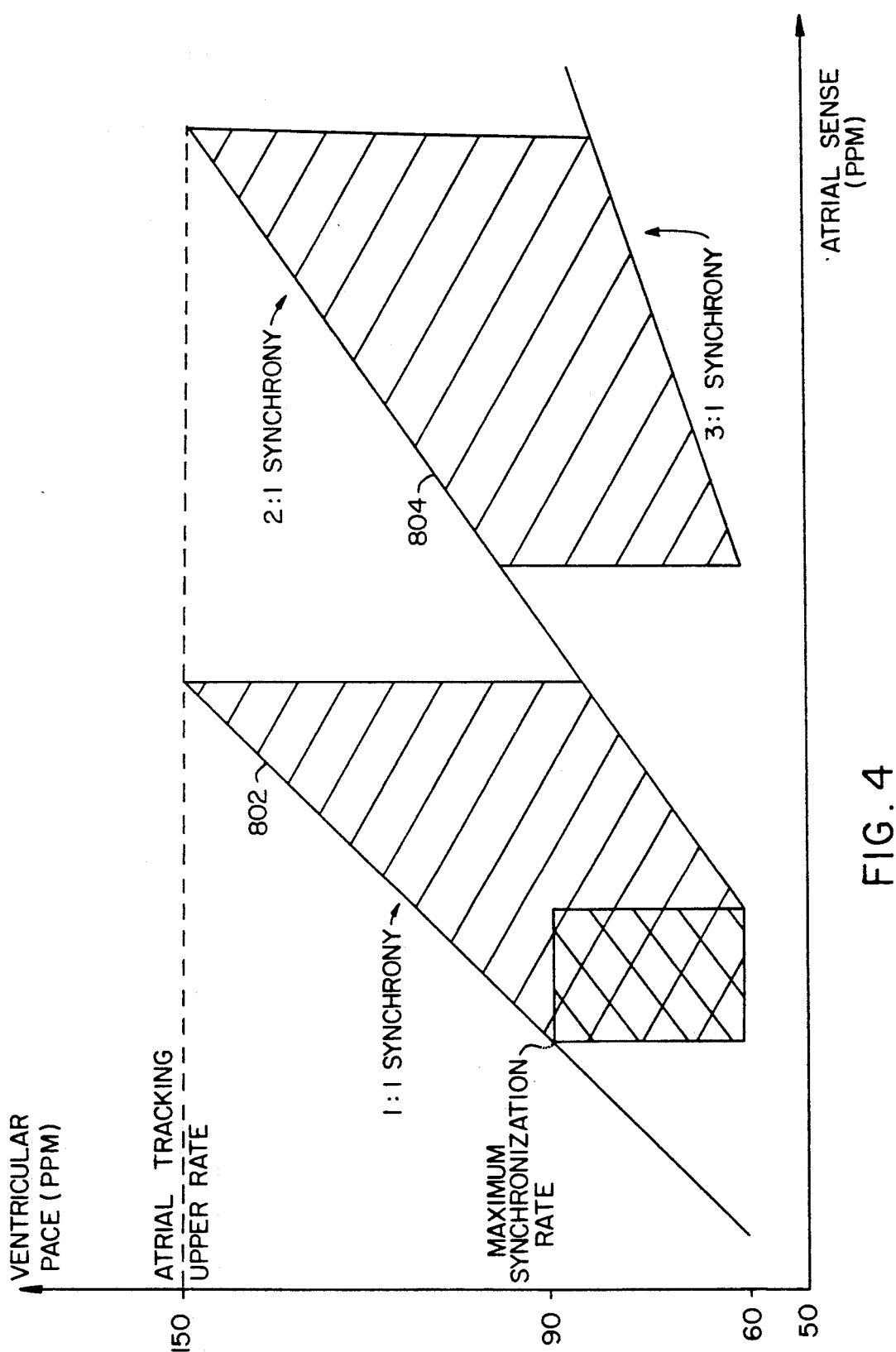
FIG. 4 is an exemplary rate diagram of the pacemaker of FIG. 1 showing the variation of the ventricular pacing change with respect to the atrial sense.

Table I exemplifies the above findings as Events 3 and 4, and FIG. 4 illustrates these events as lines 802 and 804, respectively.

If at 212 it is determined that the activity interval is greater than the VV interval, then, as indicated by block 220, the control circuit 16 compares the PP interval to the maximum synchronization interval. As defined herein, the maximum synchronization interval is defined as the sum of the AV interval and the post ventricular atrial refractory period (PVARP). PVARP is the blanking period after a ventricular sensed or paced event, during which the pacemaker 10 cannot sense an atrial event. The purpose of this blanking period is to prevent the atrial sensing circuit from detecting ventricular signals and retrogradely conducted signals.

If the PP interval is greater than, or equal to, the maximum synchronization interval, then 1 to 1 tracking (block 222) will prevail (Event 5), until the PP interval is shorter than the maximum synchronization interval (block 224), at which time the pacemaker 10 will slow its rate of ventricular pacing by 2 to 1 block (Event 6). This can be done by prolonging the PVARP for one beat.

Therefore, in these Events 5 and 6, even though atrial depolarization is sensed prior to the timing out of the activity sensor, the activity timer is allowed to time out up to a ventricular sensed event or a ventricular paced event, and the activity interval is compared to the to the VV interval. If the PP interval is longer than the maximum synchronization interval, which is defined by the atrial refractory period, atrio-ventricular synchronous pacing will occur (Event 5).

The PVARP is prolonged for one beat if the activity does not time out at a ventricular event. The PVARP prolongation defines the maximum synchronization interval. If an atrial event occurs during the PVARP, it will not result in ventricular pacing (Event 6).

In Event 6, the activity time out point is considered to be too distant from the sensed P-wave, such that the sensed atrial depolarization is treated as an atrial arrythmia or retrograde atrial event, and is ignored. As a result, the pacemaker 10 uses activity-sensing to differentiate true exercise induced sinus tachycardia from atrial arrhythmias and retrograde atrial events, and permits a selective ventricular rate control.

In the preferred embodiment, the 2 to 1 block is induced by prolonging the PVARP after the ventricular event for one cardiac cycle. For instance, the PVARP can be of the order of 200 milliseconds, and the prolonged PVARP period can be of the order of 400 milliseconds. It should however become apparent to the persons skilled in the art that other PVARP values could be selected between appropriate ranges to accomplish similar results. The PVARP could be prolonged from one value to another value in a single step increment, or it could be prolonged in a series of incremental steps. By way of an alternative, the PVARP could be modulated as a function of the rate difference between the sinus rate and the activity rate.

While in the above example the PVARP has been prolonged to accomplish the desired result, it should be understood that the atrial refractory period (ARP) could alternatively be prolonged to accomplish similar results.

While particular embodiments of the present invention have been disclosed, it is to be understood that various different modifications are possible and are contemplated within the scope of the specification, drawings, abstract and appended claims.

What is claimed is:

1. A cardiac pacemaker, comprising:

atrial sensing means for sensing depolarizations of the atrium;

ventricular sensing means for sensing depolarizations of the ventricle;

ventricular pulse generating means for generating ventricular pacing pulses;

A-V delay timer means for timing an A-V interval initiated in response to sensing of an atrial depolarization by said atrial sensing means and for triggering generation of an atrial synchronized ventricular pacing pulse by said ventricular pulse generating means on expiration of said A-V interval, said atrial synchronized ventricular pacing pulses thereby being generated separated by intervals corresponding to intervals separating said sensed atrial depolarizations;

V-V interval timing means for timing a V-V interval following generation of a ventricular pacing pulse by said ventricular pulse generating means and for triggering said ventricular pulse generating means to generate a ventricular pacing pulse at the expiration of said V-V interval;

sensor means for sensing metabolic demand and for defining a variable sensor interval corresponding to a sensor indicated pacing rate in response said sensed metabolic demand and for varying the duration of said V-V interval in correspondence with said sensor interval; and refractory interval means for timing a variable refractory period following an atrial synchronized ventricular pacing pulse, for preventing an atrial depolarization occurring therein from causing said pacemaker to initiate timing of a said A-V interval, said refractory interval means comprising means for comparing the interval separating two said atrial depolarizations prior to delivery of an atrial synchronized ventricular pacing pulse and said sensor interval in effect prior to delivery of said ventricular pacing pulse and for extending the duration of said refractory interval following each ventricular pacing pulse prior to which said interval separating said atrial depolarizations is less than V-V interval in correspondence with said sensor interval by at least a predetermined amount.

2. A pacemaker according to claim 1 further comprising atrial pulse generating means for generating atrial pacing pulses and wherein said V-V interval timing means comprises means for timing a V-A interval following generation of a ventricular pacing pulse by said ventricular pulse generating means and for triggering said atrial pulse generating means to generate an atrial pacing pulse at the expiration of said V-A interval and means for initiating timing of said A-V interval in response to generation of a said atrial pacing pulse.

3. A cardiac pacemaker according to claim 2, wherein said sensor comprises means for varying said V-A interval in response to said sensed metabolic demand, whereby said V-V interval is also varied in response to said sensed metabolic demand.

4. A pacemaker according to claim 3 wherein said V-A interval equals said sensor interval.

5. A pacemaker according to claim 4 wherein said means for comparing the interval separating said two atrial depolarizations prior to delivery of an atrial synchronized ventricular pacing pulse and said sensor interval in effect prior to delivery of said atrial synchronized ventricular pacing pulse comprises means for comparing the interval between the delivery of said atrial synchronized ventricular pacing pulse and a preceding atrial synchronized ventricular pacing pulse to said sensor interval.

6. A pacemaker according to claim 3 or 4 or 5 wherein said comparing means comprises means responsive to the expiration of a said A-V interval prior to expiration of a said V-A interval, and wherein in response to said A-V interval expiring prior to said V-A interval, said refractory interval timing means extends the duration of said atrial refractory interval following the expiration of said A-V interval.

7. A cardiac pacemaker, comprising:
atrial sensing means for sensing depolarizations of the atrium;
ventricular sensing means for sensing depolarizations of the ventricle;
ventricular pulse generating means for generating ventricular pacing pulses;
AV delay timer means for timing an AV interval initiated in response to sensing of atrial depolarization by said atrial sensing means and for triggering generation of an atrial synchronized ventricular pacing pulse by said ventricular pulse generating means on expiration of said AV interval, said atrial synchronized ventricular pacing pulses thereby being generated separated by intervals corresponding to the rate of said sensed atrial depolarizations;
V-V interval timing means for timing a V-V interval following generation of a ventricular pacing pulse by said ventricular pulse generating means and following sensing of a ventricular depolarization by said ventricular sensing means and for triggering said ventricular pulse generating means to generate a ventricular pacing pulse at the expiration of said V-V interval;
sensor means for sensing metabolic demand and for defining a variable sensor interval corresponding to a sensor indicated pacing rate in response thereto and for varying the duration of said V-V interval in correspondence with said sensor interval; and
synchronization control means for defining a variable maximum synchronization interval for 1:1 generation of atrial synchronized ventricular pacing pulses in response to atrial depolarizations, and for providing 2:1 generation of atrial synchronized ventricular pacing pulses in response to atrial depolarizations occurring more closely spaced than said maximum synchronization interval, said control means comprising means for comparing the rate of two said atrial depolarizations immediately preceding delivery of an atrial synchronized ventricular pacing pulse and said sensor indicated pacing rate in effect immediately prior to delivery of said atrial synchronized ventricular pacing pulse and for defining an increased maximum synchronization interval in effect for one V-V interval, following each atrial synchronized ventricular pacing pulse prior to which said rate of said atrial depolarizations is greater than V-V interval in correspondence with said sensor interval indicated pacing rate by at least a predetermined amount.

8. A pacemaker according to claim 7 further comprising atrial pulse generating means for generating atrial pacing pulses and wherein said V-V interval timing means comprises means for timing a V-A interval following generation of a ventricular pacing pulse by said ventricular pulse generating means and for triggering said atrial pulse generating means to generate an atrial pacing pulse at the expiration of said V-A interval and for initiating timing of said A-V interval in response to generation of a said atrial pacing pulse.

9. A cardiac pacemaker according to claim 8, wherein said sensor comprises means for varying said V-A interval in response to said sensed metabolic demand, whereby said V-V interval is also varied in response to said sensed metabolic demand.

10. A pacemaker according to claim 9 wherein said V-A interval equals said sensor interval.

11. A pacemaker according to claim 10 wherein said means for comparing the interval separating two said atrial depolarizations prior to delivery of an atrial synchronized ventricular pacing pulse and said sensor interval in effect prior to delivery of said atrial synchronized ventricular pacing pulse comprises means for comparing the interval between the delivery of said atrial synchronized ventricular pacing pulse and a preceding ventricular atrial synchronized pacing pulse to said sensor interval.

12. A pacemaker according to claim 9 or 10 or 11 wherein said comparing means comprises means responsive to the expiration of a said A-V interval prior to expiration of a said V-A interval, and wherein in response to said A-V interval expiring prior to said V-A interval, said synchronization control means defines said increased maximum synchronization interval.

13. A pacemaker according to claim 9 or 10 or 11 wherein said synchronization control means comprises means for defining a variable refractory period following an atrial synchronized ventricular pacing pulse, for preventing an atrial depolarization occurring therein from causing said pacemaker to initiate timing of a said A-V interval, and wherein said maximum synchronization interval corresponds to the sum of said A-V interval and said variable refractory interval.

* * * * *